United States Patent [19]
Bechtold

[11] Patent Number: 6,126,861
[45] Date of Patent: Oct. 3, 2000

[54] STABILIZER COMPOSITION

[75] Inventor: Karl Bechtold, Schliengen, Germany

[73] Assignee: Clariant Finance (BVI) Limited, Tortola, Virgin Islands (Br.)

[21] Appl. No.: 09/171,115

[22] PCT Filed: Apr. 10, 1997

[86] PCT No.: PCT/IB97/00388

§ 371 Date: Oct. 13, 1998

§ 102(e) Date: Oct. 13, 1998

[87] PCT Pub. No.: WO97/39051

PCT Pub. Date: Oct. 23, 1997

[30] Foreign Application Priority Data

Apr. 12, 1996 [GB] United Kingdom .................... 9607565

[51] Int. Cl.[7] ........................ C09K 15/16; C09K 15/22; C08L 5/35; C08K 5/34; C08J 5/35
[52] U.S. Cl. ................ 252/401; 252/403; 524/96; 524/99; 524/100; 524/102; 524/103
[58] Field of Search ................ 524/99, 96, 100, 524/102, 103; 252/403, 401

[56] References Cited

U.S. PATENT DOCUMENTS

| | | | |
|---|---|---|---|
| 4,863,981 | 9/1989 | Gugumus | 524/97 |
| 4,876,299 | 10/1989 | Avar | 524/99 |
| 5,679,733 | 10/1997 | Malik et al. | 524/99 |
| 5,874,493 | 2/1999 | Webster | 524/102 |

*Primary Examiner*—Jill Warden
*Assistant Examiner*—Monique T. Cole
*Attorney, Agent, or Firm*—Susan S. Jackson; Scott E. Hanf

[57] ABSTRACT

The invention relates to novel compositions of photoreactive, UV-light absorbing, low molecular weight polyalkylpiperidines and non-photoreactive low molecular weight sterically hindered polyalkylpiperidines as well as to masterbatch compositions comprising the novel compositions. The invention relates further to a process for enhancing the light stability of organic material, the stabilized organic material and its use.

23 Claims, No Drawings

STABILIZER COMPOSITION

The invention relates to novel compositions of photoreactive, low molecular weight polyalkylpiperidines and non-photoreactive low molecular weight sterically-hindered polyalkylpiperidines as well as to masterbatch compositions comprising the novel compositions and a process for stabilizing natural or synthetic organic polymeric or prepolymeric substrates against the damage effected by light, heat and/or oxidation. The invention also relates to the corresponding stabilized organic material and its use in the production of fibers and yarn, moldings, foamed plastic, coatings, lacquers or varnishes, adhesives and fabric.

According to the invention there is provided a composition, particularly suitable as light stabilizer, consisting of a photoreactive, UV-light absorbing, low molecular weight polyalkylpiperidines of general formula I (hereinafter referred to as component A)

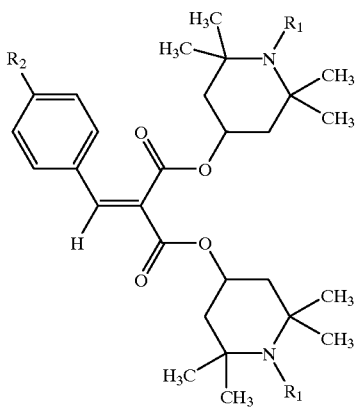

I wherein $R_1$ signifies hydrogen, hydroxyl, $C_{1-20}$alkyl, $C_{1-20}$alkoxy, or alkyl $R_2$ signifies hydrogen, $C_{1-8}$alkyl, $C_{1-2}$alkoxy and a non-photoreactive, low molecular weight sterically hindered polyalkylpiperidine (hereinafter referred to as component B) selected from the group consisting of the compounds B-1 to B-24 of the following general formulae

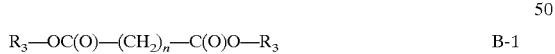 B-1

 B-2

 B-3

 B-4

 B-5 wherein $R_3$ signifies a group selected from the group consisting of (a) to (g)

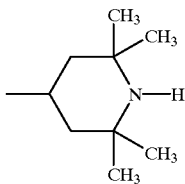 (a)

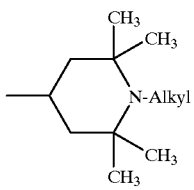 (b)

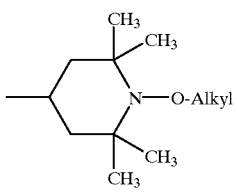 (c)

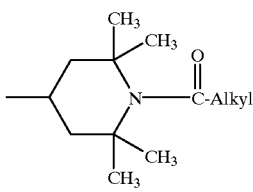 (d)

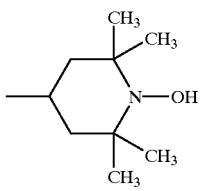 (e)

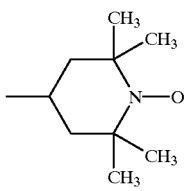 (f)

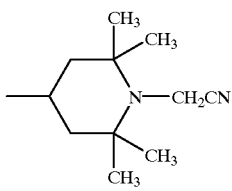 (g)

wherein alkyl signifies linear or branched or cyclic saturated $C_{1-8}$alkyl group or linear or branched or cyclic $C_{1-18}$ unsaturated group (alkenyl group)

n is an integer selected from 0 to 20, preferably 1–14, more preferably 1–10.

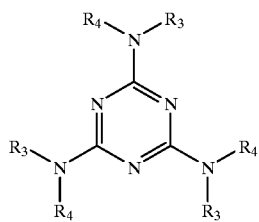

B-6 wherein $R_4$ signifies hydrogen, $C_{1-20}$alkyl, preferably $C_{1-10}$alkyl, more preferably $C_{1-4}$alky, or

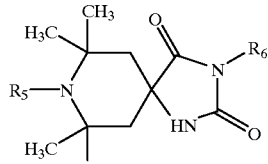

B-7

X signifies oxygen, N—$R_4$

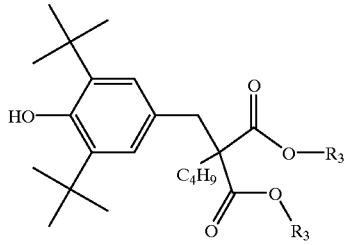

B-8

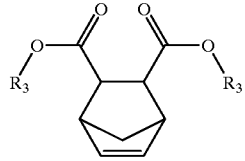

B-9

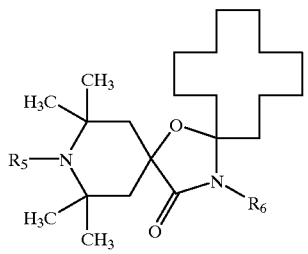

B-10 wherein $R_5$ signifies hydrogen, $C_{1-20}$alkyl, hydroxyl, $C_{1-20}$alkoxy, acyl $R_6$ signifies hydrogen, $C_{1-20}$alkyl, —CH$_2$

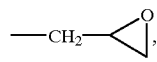, $(CH_2)_m COOR_7$, wherein m is an integer selected from 0 to 10, preferably 0–2, and $R_7$ is $C_{1-20}$alkyl

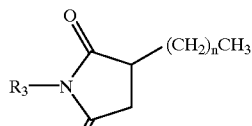

B-11

$R_3$—NH—C(O)—(CH)$_n$—C(O)—NH—$R_3$    B-12

$R_3$—N$R_4$—(CH$_2$)$_m$COOR$_7$    B-13

$R_3$—OC(O)CH$_2$CH[C(O)OR$_3$]CH[C(O)OR$_3$]CH$_2$C(O)O—$R_3$    B-14

$R_3$—OC(O)(CH$_2$)$_n$—CH$_3$    B-15

$R_3$OC(O)—Aryl    B-16

$(R_3)_3$P    B-17

$(R_3)_2$PR    B-18

$R_3$PRR    B-19

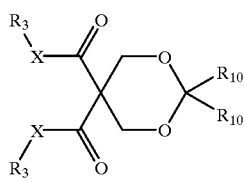

B-20

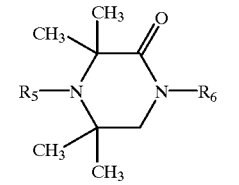

B-21

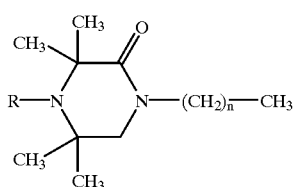

B-22 wherein $R_{10}$ signifies hydrogen, $C_{1-10}$alkyl, $C_{1-10}$alkenyl

R signifies hydrogen, $C_{1-20}$alkyl, alkoxy, —C(O)alkyl, —OC(O)alkyl or

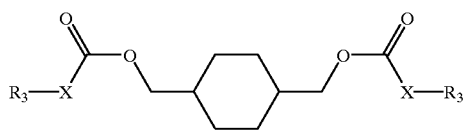

wherein n is a integer selected from 1 to 19

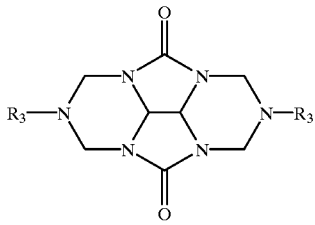

B-23

B-24

The ratio of component A to component B can be chosen within wide limits. However, a synergistic effect has been observed when the A to B ratios are 95:5 to 5:95, preferably 75:25 to 25:75, more preferably 65:35 to 35:65.

The compounds of component A and of component B are known or may be made from known compounds by known methods. Further, in this specification, where a range is given, the figures defining the range are included. Any group capable of being linear, branched or cyclic is linear, branched or cyclic unless indicated to the contrary. Also in this specification, where a symbol appears more than once in a formula, its significances are independent of one another unless indicated to the contrary.

In formula I $R_1$ signifies preferably $C_{1-8}$alkyl, formyl, acetyl, propionyl, $C_8$alkoxy.

$R_2$ in formula I signifies preferably methoxy.

In a preferred embodiment of the invention in formula I of component A $R_1$ signifies methyl and $R_2$ signifies methoxy.

In preferred compositions according to the invention component B is selected from a group consisting of the following compounds (1) to (6).

(1) a compound of formula B-1 wherein n is 8 and $R_3$ signifies

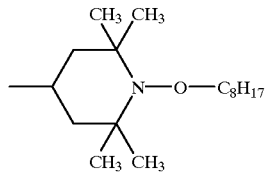

(2) a compound of formula B-1 wherein n is 8 and $R_3$ signifies

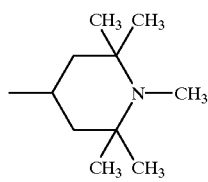

(3) a compound of formula B-1 wherein n is 8 and $R_3$ signifies

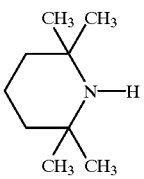

(4) a compound of formula B-10 wherein $R_5$ signifies hydrogen and $R_6$ signifies $(CH_2)_m COOR_7$ wherein m is 2 and $R_7$ is a mixture of $C_{12}H_{25}$ and $C_{14}H_{29}$ in the ratio 60 to 40.

(5) a compound of formula B-10 wherein $R_5$ and $R_6$ signify hydrogen.

(6) a compound of formula B-15 wherein n is 11 to 17 and $R_3$ signifies

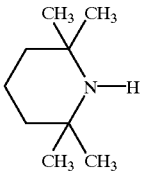

Further, particularly useful compounds of component B are as listed below.

Bis(2,2,6,6-tetramethyl-4-piperidinyl)succinate
Bis(2,2,6,6-tetramethyl-4-piperidinyl)sebacate
Bis(1,2,2,6,6-pentamethyl-4-piperidinyl)sebacate
Bis(1-octyloxy-2,2,6,6-tetramethyl-4-piperidinyl) succinate
Bis(1-octyloxy-2,2,6,6-tetramethyl-4-piperidinyl) sebacate
Tetrakis(2,2,6,6-tetramethyl-4-piperidinyl)-1,2,3,4-butane-tetracarboxylate1,1'-(1,2-Ethanediyl)bis-(3,3,5,5-tetramethylpiperazinone)
1-N-Isopropyl-3,3,5,5-tetramethyl-2-piperazinone
2,2,6,6-Tetramethyl-4-piperidinylbenzoate
2,2,6,6-Tetramethyl-4-piperidinylstearate
Bis(1,2,2,6,6-pentamethyl-piperidyl)-2-$^n$butyl-2-(2-hydroxy-3,5-di$^{tert}$butyl-benzyl)malonate
3-$^n$Octyl-7,7,9,9-tetramethyl-1,3,8-triazaspiro[4.5] decane-2,4-dione
8-Acetyl-3-dodecyl-7,7,9,9-tetramethyl-1,3,8-triazaspiro [4.5]decane-2,4-dione
3-Dodecyl-1-(2',2',6',6'-tetramethyl-4'-piperidyl)-pyrrolidin-2,5-dione
3-Dodecyl-1-(1',2',2',6',6'-pentamethyl-4'-piperidyl)-pyrrolidin-2,5-dione
3-Dodecyl-1-(1'-acetyl-2',2',6',6'-tetramethyl-4'-piperidyl)-pyrrolidin-2,5-dione
N-(2,2,6,6-tetramethyl-4-piperidinyl)-glycine-($C_1$–$C_{20}$) alkylester
N,N'-1,6-Hexanediylbis[N-(2,2,6,6-tetramethyl-4-piperidinyl)-formamide]
Hexahydro-2,6-bis(2,2,6,6-tetramethyl-4-piperidinyl)-1H,4H,5H,8H-2,3a,4a,6,7a,8a-hexaazacyclopenta[def] fluorene-4,8-dione
2,2,4,4-Tetramethyl-7-oxa-3,20-diaza-dispiro[5.1.11.2] heneicosan-21-on 2,2,4,4-Tetramethyl-7-oxa-3,20-diaza-dispiro[5.1.11.2]
heneicosan-21-on-20-propanoic acid dodecyl ester 1,5-Dioxaspiro[5.5]undecane-3,3-dicarboxylic acid bis(2,2,6,6-tetramethyl-4-piperidinyl)-ester 1,5-Dioxaspiro[5.5]undecane-3,3-dicarboxylic acid bis(1,2,2,6,6-pentamethyl-4-piperidinyl)-ester 1,5-Dioxaspiro[5.5]undecane-3,3-dicarboxylic acid bis(1-acetyl-2,2,6,6-tetra-methyl-4-piperidinyl)-ester Tris(1,2,2,6,6-pentamethyl-4-piperidinyl)phosphite 2-Methyl-2(2",2",6",6"-tetramethyl-4"-piperidinylamino)-N-(2',2',6',6'-tetra-methyl-4'-piperidinyl)propionylamide Glycine-N,N-bis[2-oxo-2-[(2,2,6,6-tetramethyl-4-piperidinyl)-oxy]ethyl]-2,2,6,6-tetramethyl-4-piperidinylester 1-[2-(3,5-Di$^{tert}$butyl-4-hydroxyphenylpropionyloxy)ethyl]-4-(3,5-di$^{tert}$butyl-4-hydroxyphenylpropionyloxy)-2,2,6,6-tetramethylpiperidine Pentakis(2,2,6,6-tetramethyl-4-piperidyl)diethylenetriamine-N,N,N',N",N"-pentaacetate According to the present invention, there is further provided a solid masterbatch composition comprising novel stabilizer compositions as hereinabove described. In such masterbatch compositions usually the amount of the stabilizer composition according to the invention is 10 to 80% by weight, preferably 15 to 40% by weight and the amount of the natural or synthetic polymeric or prepolymeric material which is identical to or compatible with the natural or synthetic polymeric or prepolymeric substrate to be stabilized is 90 to 20% by weight, preferably 85 to 60% by weight.

The invention further provides a process for enhancing the light stability of natural or synthetic polymeric or prepolymeric substrates, comprising the incorporation therein of a stabilizing quantity of a stabilizer composition as hereinabove described as such or in form of a solid masterbatch composition. The quantity of composition needed to confer an appreciable extent of light stabilization on a substrate varies with the type and end-use of the substrate. The skilled person can readily ascertain the appropriate quantity for any given case, but typical quantities are from 0.01 to 7.5% by weight, preferably from 0.03 to 5% by weight, more preferably 0.2 to 3.5% by weight.

The stabilizer composition according to the invention may be incorporated by known methods into the substrate to be stabilized before or after the polymerization, for example by melt-mixing, if appropriate with further additives before or during the shaping process, or by applying the dissolved or dispersed stabilizer composition on to the substrate, if appropriate with subsequent evaporation of the solvent.

The invention further provides a stabilized organic material comprising a light-stabilizing quantity of a composition as hereinabove described and a natural or synthetic polymeric or prepolymeric substrate. This substrate or the stabilized organic material is subjected to a shaping process, as mentioned above, which comprises the production of the whole gamut of polymeric articles, for example fibers, yarn, fabric, moldings, foam, coatings, lacquers, varnishes or adhesives.

Examples of the substrate to be stabilized are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyefins, i.e. the polymers of monoolefins exemplified in the preceding paragraph, preferably polyethylene and polypropylene, can be prepared by different, and especially by the following methods:

a) radical polymerization (normally under high pressure and at elevated temperature)

b) catalytic polymerization using a catalyst that normally contains one or more than one metal of groups IVb, Vb, VIb or VIII of the Periodic Table. These metals usually have one or more than one ligand, typically oxides, halides, alcoolates, esters, ethers, amines, alkyls, alkenyls and/or aryls that may be either π- or σ-coordinated. These metal complexes may be in the free form or fixed on substrates, typically on activated magnesium chloride, titanium (III)-chloride, alumina or silicon oxide. These catalysts may be soluble or insoluble in the polymerization medium. The catalysts can be used themselves in the polymerization or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Philips, Standard Oil Indiana, Ziegler(-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidenenorbornene; and mixtures of such copolymers with one another and with polymers mentioned in 1) above, for example polypropylene/ethylenepropylene copolymers, LDPE/ethylenevinyl acetate copolymers (EVA), LDPE/ethyleneacrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyle acrylate, styrene/butadiene/alkyl methacrylate, styrene/maleic anhydride, styrene/acrylonitrile/methyl acrylate: mixtures of high impact strength of styrene copolymers and another polymer, for example a polyacrylate, a diene polymer or an ethylene/propylene/diene terpolymer, and block copolymers of styrene such as styrene/butadiene/styrene, styrene/isoprene/styrene, styrene/ethylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers: styrene and acrylonitrile (or methacrylonitrile) on polybutadiene: styrene, acrylonitrile and methyl methacrylate on polybutadiene: styrene and maleic anhydride on polybutadiene: styrene, acrylonitrile and maleic anhydride or maleimide on polybutadiene: styrene and maleimide on polybutadiene: styrene and alkyl acrylates or methacrylates on polybutadiene: styrene and acrylonitrile on ethylene/polypropylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinyl-idene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acryl-onitrile/alkyl acrylate copolymers, acrylonitrile/alkoxyalkyl acrylate or acryl-onitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer, polyacetals modified with thermoplastic polyurethanes, acrylates or MBS.

14. Polyphenylene oxides and sulfides, and mixtures of polyphenylene oxides with styrene polymers of polyamides.

15. Polyurethanes derived from hydroxyl-terminated polyethers, polyesters of polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylene-diamine and isophthalic or/and terephthalic acid and with or without an elastomer as modifier, for example poly-2,4,4-trimethylhexamethylene terephthalamide or poly-m-phenylene isophthal-amide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bis-glycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as resins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally accruing and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex of carboxylated styrene/butadiene copolymers.

Further additives, if appropriate, can be added. Examples are given in the following.

1. Antioxidants 1.1 Alkylated monophenols, for example, 2,6-di-tert-butyl-4-methylphenol, 2-tert-butyl-4,6-dimethylphenol, 2,6-di-tert-butyl-4-ethylphenol, 2s,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-di-octadecyl-4-methylphenol, 2,4,6-tricyclohexylphenol, 2,6-di-tert-butyl-4-methoxymethylphenol, 2,6-di-nonyl-4-methylphenol, 2,4-di-methyl-6-(1'-methylunde-1'-yl)phenol, 2,4-di-methyl-6-(1'-methylheptadec-1'-yl)phenol, 2,4-dimethyl-6-(1'-methyltridec-1'-yl)phenol and mixtures thereof.

1.2 Alkylthiomethylphenols, for example, 2,4-dioctylthiomethyl-6-tert-butylphenol, 2,4-dioctylthiomethyl-6-methylphenol, 2,4-dioctylthio-methyl-6-ethylphenol, 2,6-di-dodecylthiomethyl-4-nonylphenol.

1.3 Hydroquinones and alkylated hydroquinones, for example, 2,6-di-tert-butyl-4-methoxyphenol, 2,5-di-tert-butylhydroquinone, 2,5-di-tert-amylhydro-quinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxy-anisole, 3,5-di-tert-butyl-4-hydroxyphenyl stearate, bis-(3,5-di-tert-butyl-4-hydroxyphenyl)adipate.

1.4 Tocopherols, for example, α-tocopherol, β-tocopherol, γ-tocopherol, δ-tocopherol and mixtures thereof (Vitamin E).

1.5 Hydroxylated thiophenyl ethers, for example, 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide.

1.6 Alkylidenebisphenols, for example, 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methyl-enebis(4-methyl-6-cyclohexylphenol, 2,2'-methylenebis(6-nonyl-4-methylphenol), 2,2'-methylenebis(4,6-di-tert-butylphenol), 2,2'-ethyl-idenebis(4,6-di-tert-butylphenol), 2,2'-ethylidenebis(6-tert-butyl-4-iso-butylphenol), 2,2'-methylenebis[6-(α-methylbenzyl)-4-nonylphenol], 2,2'-methylenebis[6-α,α-dimethylbenzyl)-4-nonylphenol], 4,4'-methyl-enebis(2,6-di-tert-butylphenol), 4,4'-methylenebis(6-tert-butyl-2-methyl-phenol), 1,1-bis(5-tert-butyl-4-hydroxy-2-methylphenyl)butane, 2,6-bis-(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glyco bis[3,3-bis-(3'-tert-butyl-4'-hydroxyphenyl)butyrate], bis(3-tert-butyl-4-hydroxy-5-methyl-phenyl)dicyclopentadiene, bis-[2-(3'-tert-butyl-2'-hydroxy-5'-methylbenzyl)-6-tert-butyl-4-methylphenyl]terephthalate, 1,1-bis-(3,5-di-methyl-2-hydroxyphenyl)butane, 2,2-bis-(3,5-di-tert-butyl-4-hydroxy-phenyl)-propane, 2,2-bis-(5-tert-butyl-4-hydroxy-2-methylphenyl)-4-n-dodecylmercaptobutane, 1,1,5,5-tetra-(5-tert-butyl-4-hydroxy-2-methylphenyl)pentane.

1.7 O-, N- and S-benzylcompounds, for example, 3,5,3',5'-tetra-tert-butyl-4,4'-dihydroxydibenzyl ether, octadecyl-4-hydroxy-3,5-dimethylbenzyl-mercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxy-benzylmercaptoacetate.

1.8 Hydroxybenzylated malonates, for example, dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)-malonate, bis-[4-(1,1,3,3-tetramethyl-butyl)phenyl]-2,2-bis(3,5-di-tert-butyl-4-hydroxybenzyl)malonate.

1.9 Aromatic hydroxybenzyl compounds, for example, 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10 Triazine compounds, for example, 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis((3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-di-methylbenzyl) isocyanurate, 2,4,6-tris(3,5-di-tert-butyl-4-hydroxyphenylethyl)-1,3,5-triazine, 1,3,5-tris((3,5-di-tert-butyl-4-hydroxy-phenylpropionyl)hexahydro-1,3,5-triazine, 1,3,5-tris(3,5-dicyclohexyl-4-hydroxybenzyl)isocyanurate.

1.11 Benzylphosphonates, for example, dimethyl-2,5-di-tert-butyl-4-hydroxybenzylphosphonate, diethyl-3,5-di-tert-butyl-4-hydroxybenzylphosphon-ate, dioctadecyl-3,5-di-tert-butyl-4-hydroxybenzylphosphonate, diocta-decyl-5-tert-butyl-4-hydroxy-3-methylbenzylphosphonate, the calcium salt of the monoethyl ester of 3,5-di-tert-butyl-4-hydroxybenzylphosphonic acid.

1.12 Acylaminophenols, for example, 4-hydroxylauranilide, 4-hydroxystear-anilide, octyl N-(3,5-di-tert-butyl-4-hydroxyphenyl)carbamate.

1.13 Esters of β-(3,5-di-tert-butyl-4-hydroxyphenyl) propionic acid with mono-or polyhydric alcohols, e.g., with methanol, ethanol, octanol, octadecanol, 1,6-hexanediol, 1,9-nonanediol, ethylene glycol, 1,2-propanediol, neopentyl glycol, thiodiethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(5-tert-butyl-4-hydroxy-3-methylphenyl) propionic acid with mono- or polyhydric alcohols, e.g., with methanol, ethanol, octanol, octa-decanol, 1,6-hexanediol, 1,9-nonanediol, ethylene glycol, 1,2-propanediol, neopentyl glycol, thiodiethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of β-(3,5-dicyclohexyl-4-hydroxyphenyl) propionic acid with mono- or polyhydric alcohols, e.g., with methanol, ethanol, octanol, octadecanol, 1,6-hexanediol, 1,9-nonanediol, ethylene glycol, 1,2-propanediol, neopentyl glycol, thiodiethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7 trioxabicyclo[2.2.2]-octane.

1.16 Esters of 3,5-di-tert-butyl-4-hydroxyphenyl acetic acid with mono- or polyhydric alcohols, e.g., with methanol, ethanol, octanol, octadecanol, 1,6-hexanediol, 1,9-nonanediol, ethylene glycol, 1,2-propanediol, neo-pentyl glycol, thiodiethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17 Amides of β-(3,5-di-tert-butyl-4-hydroxyphenyl) propionic acid, e.g. N,N'-bis(3,5-di-tert-butyl-4-hydroxyphenylpropionyl)hexamethylene-diamine, N, N'-bis(3,5-di-tert-butyl-4-hydroxyphenylpropionyl)hydrazine.

2. UV absorbers and other light stabilizers 2.1 2-(2'-Hydroxyphenyl)benzotriazoles, for example, 2-(2'-hydroxy-5'-methylphenyl)-benzotriazole, 2-(3',5'-di-tert-butyl-2'-hydroxyphenyl)-benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)5-chloro-benzotriazole, 2-(3'-sec-butyl-5'-tert-butyl-2'-hydroxyphenyl)benzotriazole, 2-(2'-hydroxy-4'-octyloxyphenyl)-benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-5'-α,α-dimethylbenzyl-2'-hydroxyphenyl)benzotriazole, mix-ture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonyl-ethyl]-2'-hydroxyphenyl)-5-chloro-benzotriazole, 2-(3'-tert-butyl-2'-hydroxy-5'-(2-methoxycarbonylethyl)phenyl)-5-chloro-benztriazole, 2-(3'-tert-butyl-2'-hydroxy-5'(2-octyloxycarbonylethyl)phenyl)benzotri-azole, 2-(3 '-tert-butyl-5'-[2-(2-ethylhexyloxy) carbonylethyl]-2'-hydroxy-phenyl)benzotriazole, 2-(3-dodecyl-2'-hydroxy-5'-methylphenyl)benzotri-azole, and 2-(3'-tert-butyl-2'-hydroxy-5'-(2-isooctyloxycarbonylethyl)-phenylbenzotriazole, 2,2'-methylene-bis[4-(1,1,3,3-tetramethylbutyl)-6-benzotriazole-2-ylphenol]; the transesterification product of 2-[3'-tert-butyl-5'(2-methoxycarbonylethyl)-2'-hydroxyphenyl]-2H-benzotriazole with polyethyleneglycol 300; [R—CH$_2$CH$_2$—COO(CH$_2$)$_3$]$_2$- where R=3'-tert-butyl-4'-hydroxy-5'-2H-benzotriazole-2-ylphenyl.

2.2 2-Hydroxybenzophenones, for example, the 4-hydroxy, 4-methoxy, 4-octy-loxy, 4-decyloxy, 4-dodecyloxy, 4-benzyloxy, 4,2',4'-trihydroxy and 2'-hydroxy-4,4'-dimethoxy derivatives.

2.3 Esters of substituted and unsubstituted benzoic acids, as for example, 4-tert-butylphenyl-salicylate, phenyl-salicylate, octylphenyl-salicylate, di-benzoyl-resorcinol, bis(4-tert-butylbenzoyl)resorcinol, benzoyl resorcin-ol, 2,4-di-tert-butylphenyl-3,5-di-tert-butyl-4-hydroxybenzoate, hexadecyl-3,5-di-tert-butyl-4-hydroxybenzoate, octadecyl 3,5-di-tert-butyl-4-hydroxybenzoate, 2-methyl-4,6-di-tert-butylphenyl-3,5-di-tert-butyl-4-hydroxybenzoate.

2.4 Acrylates, for example, ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5 Nickel compounds, for example, nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethenolamine, nickel dibutyldithiocarbamate, nickel salts of the monoalkyl esters, e.g. the methyl or ethyl ester of 4-hydroxy-3,5-di-tert-butyl-benzylphosphonic acid, nickel complexes of ketoximes, e.g. of 2-hydroxy-4-methylphenyl undecylketoxime, nickel complexes of 1-phenyl-4-lauroyl-5-hydroxyrazole, with or without additional ligands.

2.6 Oxamides, for example, 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylamino-propyl)oxanilide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of ortho- and para-ethoxy-disubstituted oxanilides.

2.7 2-(2-Hydroxyphenyl)1,3,5-triazines, for example, 2,4,6-tris(2-hydroxy-4-octyloxyphenyl)-1,3,5-triazine, 2-(2-hydroxy-4-octyloxyphenyl)-4,6-bis-(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxy-phenyl)-6-(2,4-dimethylphenyl)-1,3,5-triazine, 2-(2-hydroxy-4-dodecyl-oxyphenyl)-4,6-bis-(4-methylphenyl)-1,3,5-triazine, 2-(2-hydroxy-4-octyl-oxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hy-droxy-4-(2-hydroxy-3-octyloxy-propyloxy)phenyl]-4,6-bis(2,4-dimethyl)-1,3,5-triazine.

3. Metal deactivators, for example, N,N'-diphenyloxamide, N-salicylayl-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis-(benzylidene)oxalyl dihydrazide, oxanilide, isophthaloyl dihydrazide, sebacoyl bisphenylhydra-zide, N,N'-diacetyladipoyl dihydrazide, N,N'-bis-(salicyloyl)-oxalyl dihydrazide, N,N'-bis(salicyloyl)-thiopropionyl dihydrazide.

4. Phosphites and phosphonites, for example, triphenyl phosphite, diphenyl alkyl phosphites, phenyl dialkyl phosphites, tris(nonylphenyl)phosphite, trilauryl phos-phite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis-(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butyl-phenyl)pentaerythritol diphosphite, tristearyl sorbitol triphosphite, tetrakis-(2,4-di-tert-butylphenyl)-4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz-[d,g]-1,3,2-dioxaphosphocin, bis(2,4-di-tert-butyl-6-methylphenyl)methylphosphite, bis(2,4-di-tert-butyl-6-methylphenyl)ethyl-phos-phite.

5. Hydroxylamines, for example, dibenzoylhydroxylamine, dioctylhydroxylamine, diodecylhydroxylamine, ditetradecylhydroxylamine, dihexadecylhydroxylamine, dioctadecylhydroxylamine, 1-hydroxy-2,2-6,6-tetramethyl-4-piperidyl benzoate or bis (1-hydroxy-2,2,6,6-tetramethyl-4-piperidyl)sebacate.

6. Peroxide scavengers, for example, esters of β-thiodipropionic acids, for example the lauryl, stearyl, myristyl or tridecyl esters, mercaptobenzimidazole or the zinc salt of 2-mercaptobenzimidazole, zinc dibutyl-dithiocarbamate, dioctadecyl di-sulfide, pentaerythritol tetrakis(β-dodecylmercapto)propionate.

7. Polyamide stabilizers, for example, copper salts in combination with iodides and/or phosphorus compounds and salts of divalent manganese.

8. Basic co-stabilizers, for example, melamine, polyvinylpyrrolidine, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or tin pyrocatecholate.

9. Nucleating agents, for example, 4-tert-butylbenzoic acid, adipic acid, diphenyl-acetic acid.

10. Fillers or reinforcing agents, for example, calcium cabonate, silicates, glass fibers, asbestos, talc, kaolin, mica, barium sulfate, metal oxides and hydroxides, carbon black, graphite.

11. Other additives, for example, plasticisers, lubricants, emulsifiers, pigments, optical brighteners, flameproofing agents, antistatic agents and blowing agents.

12. Benzofuranones and indolinones, for example, those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4 316 611, DE-A-4 316 622, DE-A-4 316 876, EP-A-0 589 839 or EP-A-0 591 102 or 3-[4-(2-acetoxyethoxy)phenyl]-5,7-di-tert-butyl-benzofuran-2-one, 5,7-di-tert-butyl-3-[4-2-stearoyloxyethoxy)phenyl]-benzofuran-2-one, 3,3'-bis-[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The invention is further illustrated by means of the following examples in which all parts are expressed by weight:

EXAMPLE 1

100 parts of polypropylene powder (melt flow index 4, 230° C./2.16 kg) are dry blended with 0.1 parts Ca-stearate, 0.05 parts of pentaerythrityl-tetrakis-[3-(3,5-di-tert-butyl-4-hydroxyphenyl)-propionate] and 0.075 parts of each component A and component B and are homogenized for 10 minutes at 220° C. The composition thus obtained is compression-molded in a toggle press to give a 1–1.5 mm thick plate. Part of the crude molding obtained is cut out and compressed between two high gloss hard aluminium foils at 210° C. for 1.5 minutes at a pressure of 3 tons and additionally for further 1.5 minutes at a pressure of 30 tons to give a 0.0 mm thick film. Portions each of about 40×45 mm are now punched from this film and irradiated in Atlas Weather-Ometer Ci 65. At regular intervals of time, these test samples are removed from the irradiation apparatus and tested for their carbonyl content in an IR spectrophotometer. The increase in the carbonyl extinction on exposure is a measure of the photooxidative degradation of the polymer and, according to experience, is associated with a deterioration in the mechanical properties of the polymer. The time taken to reach a carbonyl-index of 0.30 is considered to be a measure of the stabilizing action.

| Composition No. | Component A | Component B |
| --- | --- | --- |
| A | Sanduvor PR 31 [(1)] | Tinuvin 770 [(2)] |
| B | Sanduvor PR 31 | Tinuvin 292 [(3)] |
| C | Sanduvor PR 31 | Tinuvin 123 [(4)] |
| D | Sanduvor PR 31 | Sanduvor 3050 [(5)] |
| E | Sanduvor PR 31 | Dastib 845 [(6)] |

1) Sanduvor PR 31 is a trade name of the company Clariant for a compound of formula I wherein $R_1$ signifies methyl and $R_2$ signifies methoxy.

2) Tinuvin 770 is a trade name of the company Ciba-Geigy for a compound of formula B-1 wherein n is 8 and $R_3$ signifies

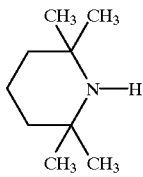

3) Tinuvin 292 is a trade name of the company Ciba-Geigy for a compound of formula B-1 wherein n is 8 and $R_3$ signifies

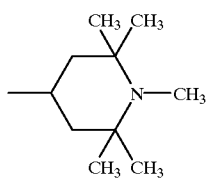

4) Tinuvin 123 is a trade name of the company Ciba-Geigy for a compound of formula B-1 wherein n is 8 and $R_3$ signifies

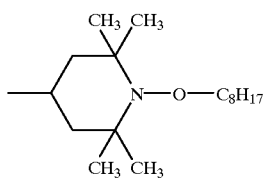

5) Sanduvor 3050 is a trade name of the company Clariant for a compound of formula B-10 wherein $R_5$ signifies hydrogen and $R_6$ signifies $(CH_2)_m COOR_7$ wherein m is 2 and $R_7$ is a mixture of $C_{12}H_{25}$ and $C_{14}H_{29}$ in the ratio of 60 to 40.

6) Dastib is a trade name of the company Vucht for a compound of formula B-15 wherein m is 11 to 17 and $R_3$ signifies

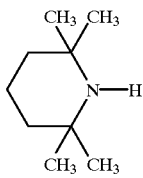

EXAMPLE 2

100 parts of polypropylene powder (Hostalen PPU 0180 P, Hoechst, MFI 15 g/10 min.; 230° C./2.16 kg) are mixed with 0.1 parts Ca-stearate, 0.05 parts pentaerythrityl-tetrakis-[3-(3,5-di-tert-butyl-4-hydroxyphenyl)-propionate] and 0.15 parts of the light stabilizers and melt-homogenized by extrusion.

Accelerated weathering was done according to the following standards:

UV-A: according to ASTM D-5208 (UVCON-device)

CAM-7: according to DIN 53387-A (Weather-Ometer Ci65)

Some of the plaques are used to produce press films of an average thickness of about 0.1 mm. These films are also submitted to accelerated weathering. Monitoring the increase of the carbonyl absorption at about 1720 cm$^{-1}$ using an IR-spectrometer at certain time intervals gives an indication of the photooxidative degradation.

The time ($T_{0.5\ measured}$) to reach the carbonyl extinction of 0.5 is given in tables 1 and 2.

The $T_{0.5\ calculated}$-values are calculated according to the additivity rule (B. Ranby and J. F. Rabek, Photodegradation, Photo-oxidation and Photostabilization of Polymers, Principles and Applications, a Wiley-Interscience Publication, 1975, pp 418–422) and using the following equation:

$$T_{0.5\ calculated} = \frac{(n-p) \times T_{0.5} HALS\ \underline{A} + p \times T_{0.5} HALS\ \underline{B}}{n}$$

The synergistic effect is determined comparing the calculated and measured $T_{0.5}$-values. The values are also given in tables 1 and 2.

A synergistic effect for the described mixtures is given if $T_{0.5\ measured} > T_{0.5\ calculated}$.

TABLE 1

Light stability in polypropylene films after UV-A irradiation

| HALS | | $T_{0.5\ measured}$ | $T_{0.5\ calculated}$ |
|---|---|---|---|
| control | | 305 | |
| 0.15% | Sanduvor PR-31 | 1775 | |
| 0.15% | Tinuvin 770 | 3060 | |
| 0.15% | Tinuvin 292 | 2040 | |
| 0.15% | Tinuvin 123 | 1920 | |
| 0.15% | Sanduvor 3050 | 1570 | |
| 0.15% | Dastib 845 | 2900 | |
| 0.05% | Sanduvor PR-31 | | |
| 0.10% | Tinuvin 770 | 2950 | 2630 |
| 0.05% | Sanduvor PR-31 | 2400 | 1950 |
| 0.10% | Tinuvin 292 | | |
| 0.05% | Sanduvor PR-31 | 1930 | 1870 |
| 0.10% | Tinuvin 123 | | |
| 0.05% | Sanduvor PR-31 | 1700 | 1630 |
| 0.10% | Sanduvor 3050 | | |
| 0.10% | Sanduvor PR-31 | 2670 | 2150 |
| 0.05% | Dastib 845 | | |

TABLE 2

Light stability in polypropylene films after Weather-Ometer CAM-7 irradiation

| HALS | | $T_{0.5\ measured}$ | $T_{0.5\ calculated}$ |
|---|---|---|---|
| control | | 520 | |
| 0.15% | Sanduvor PR-31 | 2470 | |
| 0.15% | Tinuvin 770 | 2500 (broken) | |
| 0.15% | Tinuvin 292 | 2320 | |
| 0.15% | Tinuvin 123 | 2090 | |
| 0.15% | Sanduvor 3050 | 2140 | |
| 0.15% | Dastib 845 | 2200 | |
| 0.05% | Sanduvor PR-31 | 2880 | 1667 |
| 0.10% | Tinuvin 770 | | |
| 0.10% | Sanduvor PR-31 | 3100 | 2480 |
| 0.05% | Tinuvin 770 | | |
| 0.05% | Sanduvor PR-31 | 2620 | 2370 |
| 0.10% | Tinuvin 292 | | |
| 0.05% | Sanduvor PR-31 | 2550 | 2216 |
| 0.10% | Tinuvin 123 | | |
| 0.05% | Sanduvor PR-31 | 2600 | 2250 |
| 0.10% | Sanduvor 3050 | | |

What is claimed is:

1. A composition consisting of a photoreactive, UV light absorbing, low molecular weight polyalkylpiperidine of formula I as component A

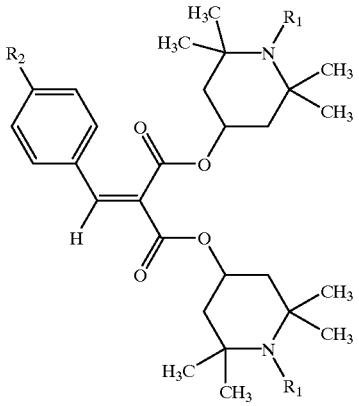

wherein $R_1$ is hydrogen, hydroxyl, $C_{1-20}$alkyl, $C_{1-20}$alkoxy, or acyl, and $R_2$ is hydrogen, $C_{1-8}$alkyl, or $C_{1-2}$alkoxy, and a non-photoreactive, low molecular weight sterically hindered polyalkyl-piperidine as component B wherein component B is a compound of formula:

$R_3$—OC(O)—(CH$_2$)$_n$—C(O)O—$R_3$  B-1;

$R_3$—NH—(CH$_2$)$_n$—NH—$R_3$  B-2;

$R_3$—OCH$_2$CH=CHCH$_2$—O—$R_3$  B-3;

$R_3$—OC(O)—NR$_3$—(CH$_2$)$_6$—NR$_3$C(O)O—$R_3$  B-4;

$R_3$—O—Si(CH$_3$)$_2$—O—$R_3$  B-5;

wherein $R_3$ is a group selected from the group consisting of:

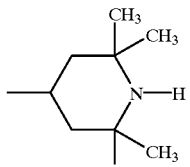

(a)

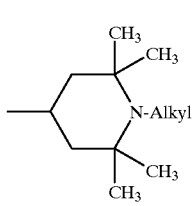

(b)

-continued (c) 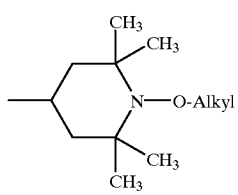

(d) 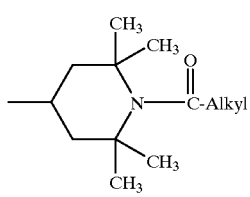

(e) 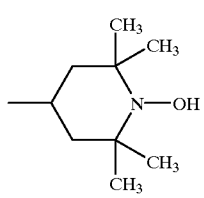

(f) 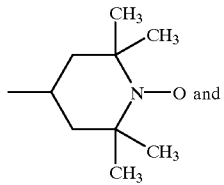

(g) 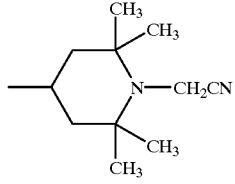

wherein

Alkyl is linear or branched or cyclic saturated $C_{1-18}$alkyl group or linear or branched or cyclic $C_{1-18}$ unsaturated group (alkenyl group), n is an integer from 0 to 20;

B-6 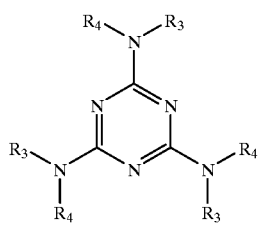

wherein $R_4$ is hydrogen, $C_{1-20}$alkyl, or $R_3$;

B-7 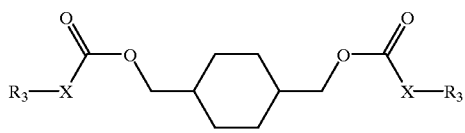

wherein

X is oxygen or N—$R_4$,

B-8 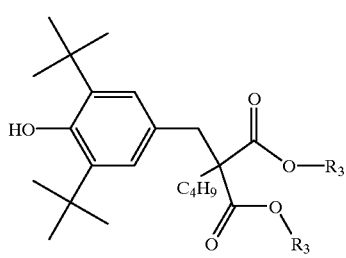

B-9 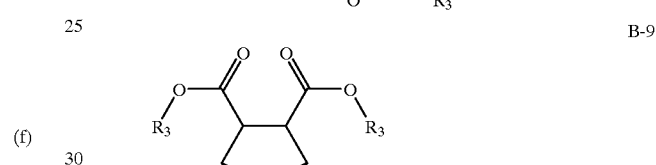

B-10 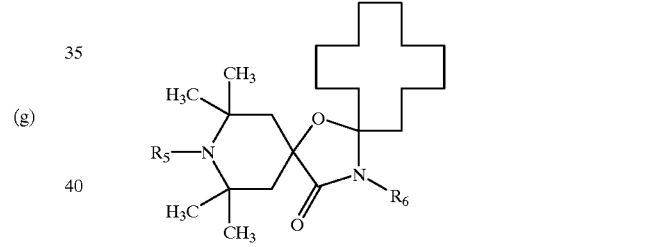

wherein $R_5$ is hydrogen, $C_{1-20}$alkyl, hydroxyl, $C_{1-20}$alkoxy, or acyl, $R_6$ is hydrogen, $C_{1-20}$alkyl,

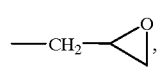

or $(CH_2)_mCOOR_7$, wherein m is an integer selected from 0 to 10, $R_7$ is $C_{1-20}$alkyl;

B-11 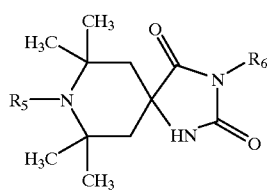

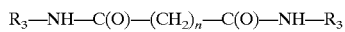 B-12;

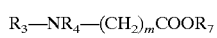 B-13;

 B-14;

 B-15;

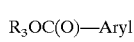 B-16;

 B-17;

 B-18;

 B-19;

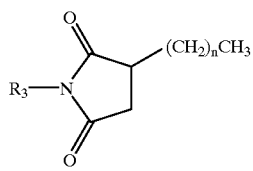 B-20

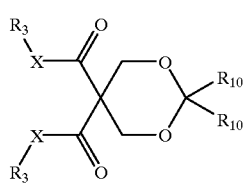 B-21

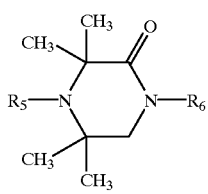 B-22 wherein
$R_{10}$ is hydrogen, $C_{1-10}$alkyl, or $C_{1-10}$alkenyl,
R is hydrogen, $C_{1-20}$alkyl, alkoxy, —C(O)alkyl, —OC(O)alkyl or

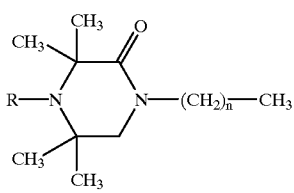

wherein n is an integer from 1 to 19;

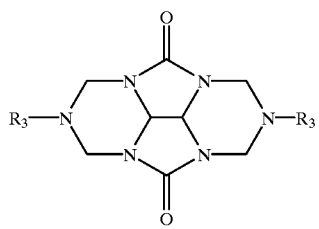 B-23 or

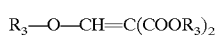 B-24.

2. The composition according to claim 1, wherein n of formulae B-1 and B-2 is an integer from 1 to 14.

3. The composition according to claim 2, wherein n of formulae B-1 and B-2 is an integer from 1 to 10.

4. The composition according to claim 1, wherein $R_4$ of formula B-6 is $C_{1-10}$alkyl.

5. The composition according to claim 4, wherein $R_4$ of formula B-6 is $C_{1-4}$alkyl.

6. The composition according to claim 1, wherein m of $(CH_2)_mCOOR_7$ is an integer from 0 to 2.

7. The composition according to claim 1, wherein A and B are in a ratio of A to B of 95:5 to 5:95.

8. The composition according to claim 7, wherein the ratio of A to B is 75:25 to 25:75.

9. The composition according to claim 8, wherein the ratio of A to B is 65:35 to 35:65.

10. A solid masterbatch composition comprising:

(a) a composition consisting of a photoreactive, UV light absorbing, low molecular weight polyalkylpiperidine of formula I as component A

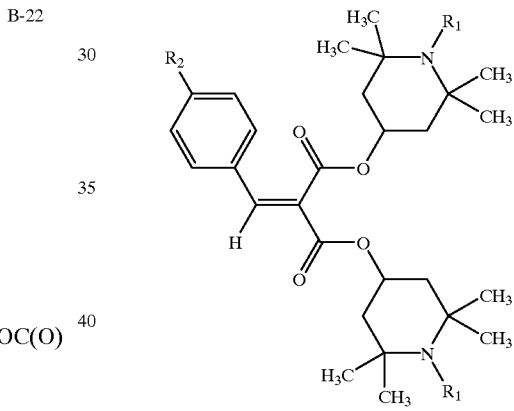 I wherein
$R_1$ is hydrogen, hydroxyl, $C_{1-20}$alkyl, $C_{1-20}$alkoxy, or acyl, and
$R_2$ is hydrogen, $C_{1-8}$alkyl, or $C_{1-2}$alkoxy, and a non-photoreactive, low molecular weight sterically hindered polyalkyl-piperidine as component B wherein component B is a compound of formula:

$R_3$—OC(O)—$(CH_2)_n$—C(O)O—$R_3$    B-1;

$R_3$—NH—$(CH_2)_n$—NH—$R_3$    B-2;

$R_3$—OCH$_2$CH=CHCH$_2$—O—$R_3$    B-3;

$R_3$—OC(O)—NR$_3$—$(CH_2)_6$—NR$_3$C(O)O—$R_3$    B-4;

$R_3$—O—Si(CH$_3$)$_2$—O—$R_3$    B-5;

wherein $R_3$ is a group selected from the group consisting of:

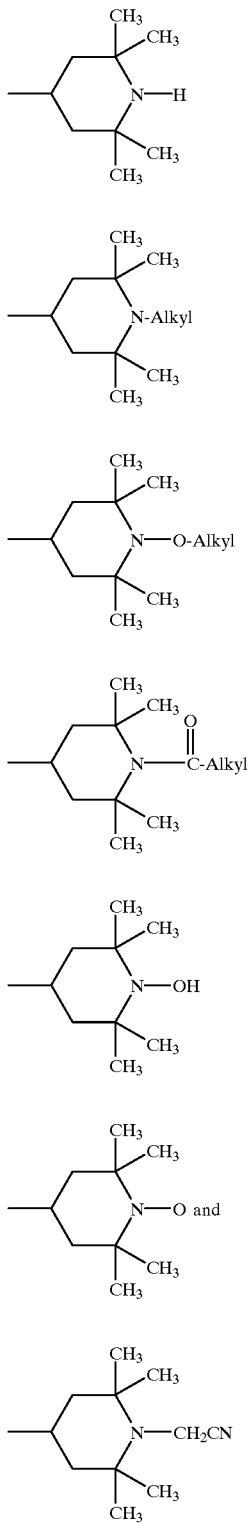

(a) N—H piperidine with 2,2,6,6-tetramethyl
(b) N-Alkyl
(c) N—O-Alkyl
(d) N—C(O)-Alkyl
(e) N—OH
(f) N—O and
(g) N—CH$_2$CN wherein Alkyl is linear or branched or cyclic saturated $C_{1-18}$alkyl group or linear or branched or cyclic $C_{1-18}$ unsaturated group (alkenyl group), n is an integer from 0 to 20;

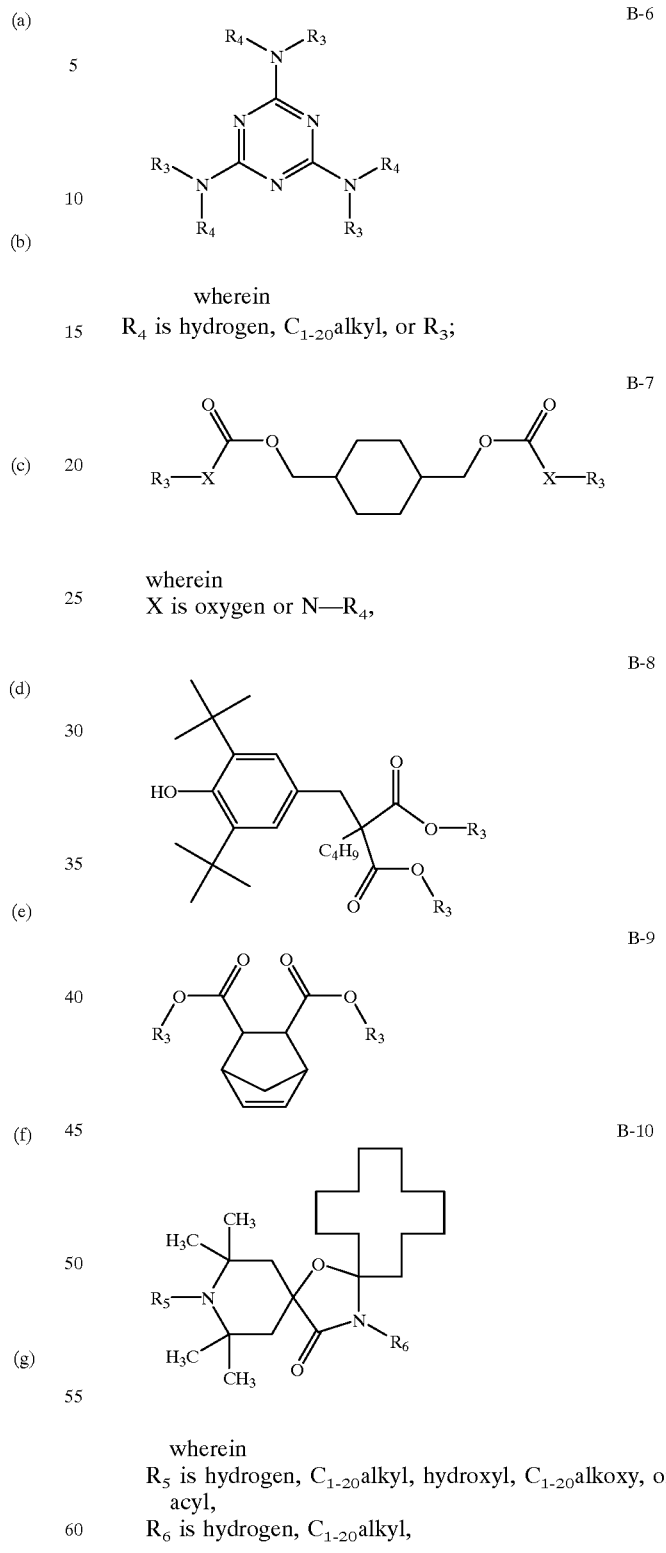

B-6 wherein
$R_4$ is hydrogen, $C_{1-20}$alkyl, or $R_3$;

B-7 wherein
X is oxygen or N—$R_4$,

B-8

B-9

B-10 wherein
$R_5$ is hydrogen, $C_{1-20}$alkyl, hydroxyl, $C_{1-20}$alkoxy, or acyl,
$R_6$ is hydrogen, $C_{1-20}$alkyl, —CH$_2$—(epoxide), or $(CH_2)_m COOR_7$, wherein m is an integer selected from 0 to 10, $R_7$ is $C_{1-20}$alkyl,

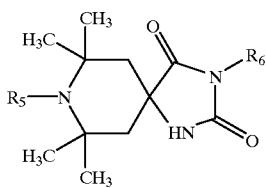
B-11

$R_3$—NH—C(O)—(CH$_2$)$_n$—C(O)—NH—$R_3$  B-12;

$R_3$—NR$_4$—(CH$_2$)$_m$COOR$_7$  B-13;

$R_3$—OC(O)CH$_2$CH[C(O)OR$_3$]CH[C(O)OR$_3$]CH$_2$C(O)O—$R_3$  B-14;

$R_3$—OC(O)(CH$_2$)$_n$—CH$_3$  B-15;

$R_3$OC(O)—Aryl  B-16;

$(R_3)_3$P  B-17;

$(R_3)_2$PR  B-18;

$R_3$PRR  B-19;

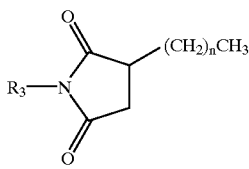
B-20

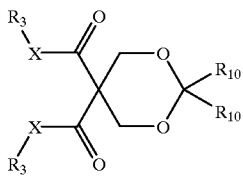
B-21

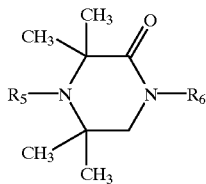
B-22 wherein
$R_{10}$ is hydrogen, $C_{1-10}$alkyl, or $C_{1-10}$alkenyl,
R is hydrogen, $C_{1-20}$alkyl, alkoxy, —C(O)alkyl, —OC(O)alkyl or

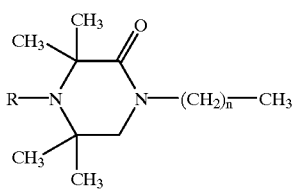

wherein n is an integer from 1 to 19;

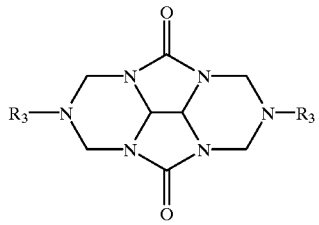
B-23 or $R_3$—O—CH=C(COOR$_3$)$_2$  B-24, and (b) a natural or synthetic polymeric or prepolymeric material which is identical to or compatible with a natural or synthetic polymeric substrate to be stabilized.

11. The solid masterbatch composition according to claim 10, comprising 10 to 80% by weight of the stabilizer composition and 90 to 20% by weight of a natural or synthetic polymeric or prepolymeric material.

12. The solid masterbatch composition according to claim 11, wherein the stabilizer composition is 15 to 40% by weight.

13. The solid masterbatch composition according to claim 11, wherein the natural or synthetic polymeric or prepolymeric material is 85 to 60% by weight.

14. A process for stabilizing a natural or synthetic polymeric or prepolymeric substrate against the damage effected by light comprising adding to the substrate a stabilizing quantity of a composition wherein the composition consists of a photoreactive, UV light absorbing, low molecular weight polyalkylpiperidine of formula I as component A

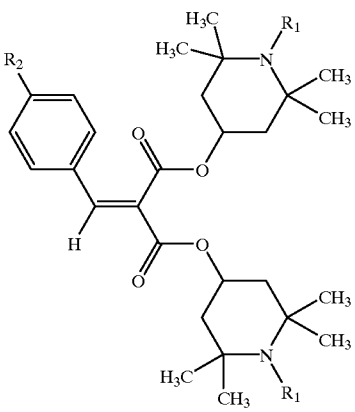
I wherein
$R_1$ is hydrogen, hydroxyl, $C_{1-20}$alkyl, $C_{1-20}$alkoxy, or acyl, and
$R_2$ is hydrogen, $C_{1-8}$alkyl, or $C_{1-2}$alkoxy,
and a non-photoreactive, low molecular weight sterically hindered polyalkyl-piperidine as component B wherein component B is a compound of formula:

$R_3$—OC(O)—(CH$_2$)$_n$—C(O)O—$R_3$  B-1;

$R_3$—NH—(CH$_2$)$_n$—NH—$R_3$  B-2;

$R_3$—OCH$_2$CH=CHCH$_2$—O—$R_3$  B-3;

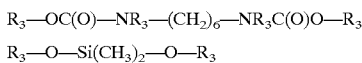 B-4;

R₃—O—Si(CH₃)₂—O—R₃    B-5;

wherein

R₃ is a group selected from the group consisting of:

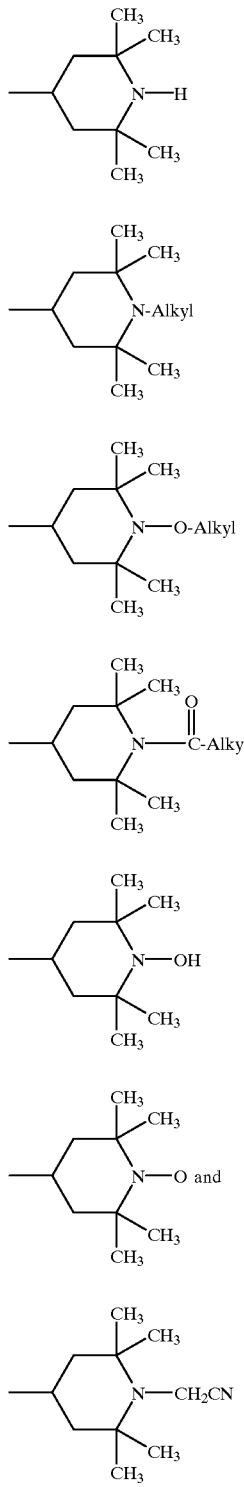

wherein

Alkyl is linear or branched or cyclic saturated $C_{1-18}$alkyl group or linear or branched or cyclic $C_{1-18}$ unsaturated group (alkenyl group), n is an integer from 0 to 20;

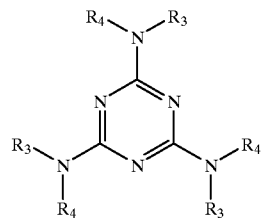 B-6 wherein

R₄ is hydrogen, $C_{1-20}$alkyl, or R₃;

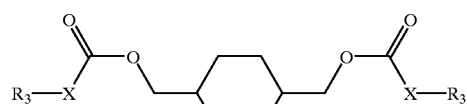 B-7 wherein

X is oxygen or N—R₄,

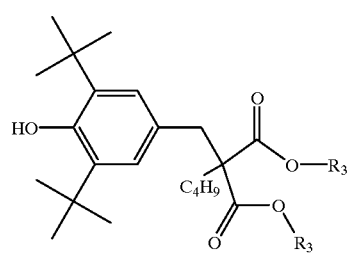 B-8

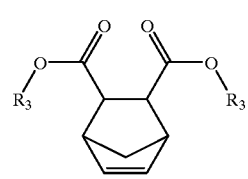 B-9

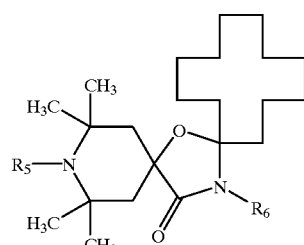 B-10

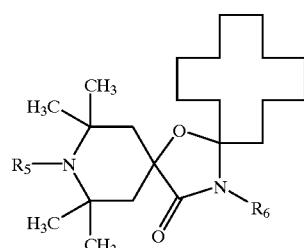

wherein

R₅ is hydrogen, $C_{1-20}$alkyl, hydroxyl, $C_{1-20}$alkoxy, or acyl, $R_6$ is hydrogen, $C_{1-20}$alkyl,

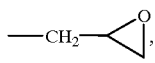

or $(CH_2)_mCOOR_7$, wherein m is an integer selected from 0 to 10, $R_7$ is $C_{1-20}$alkyl;

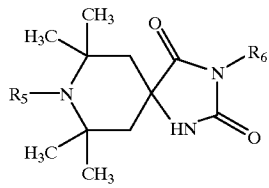  B-11

| | |
|---|---|
| $R_3$—NH—C(O)—$(CH_2)_n$—C(O)—NH—$R_3$ | B-12; |
| $R_3$—$NR_4$—$(CH_2)_m$COOR$_7$ | B-13; |
| $R_3$—OC(O)CH$_2$CH[C(O)OR$_3$]CH[C(O)OR$_3$]CH$_2$C(O)O—$R_3$ | B-14; |
| $R_3$—OC(O)$(CH_2)_n$—CH$_3$ | B-15; |
| $R_3$OC(O)—Aryl | B-16; |
| $(R_3)_3$P | B-17; |
| $(R_3)_2$PR | B-18; |
| $R_3$PRR | B-19; |

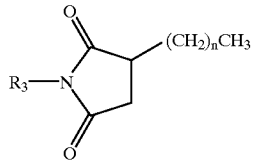 B-20

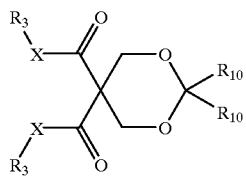 B-21

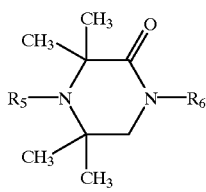 B-22 wherein $R_{10}$ is hydrogen, $C_{1-10}$alkyl, or $C_{1-10}$alkenyl,

R is hydrogen, $C_{1-20}$alkyl, alkoxy, —C(O)alkyl, —OC(O)alkyl or

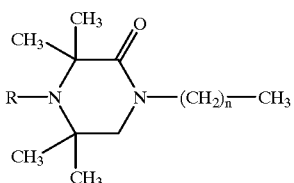

wherein n is an integer from 1 to 19;

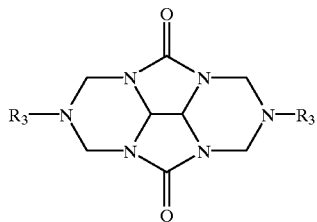 B-23 or $R_3$—O—CH=C(COOR$_3$)$_2$  B-24.

15. A process for stabilizing a natural or synthetic polymeric or prepolymeric substrate against the damage effected by light comprising adding to the substrate a stabilizing quantity of a solid masterbatch composition wherein the solid masterbatch composition comprises:

(a) a composition consisting of a photoreactive, UV light absorbing, low molecular weight polyalkylpiperidine of formula I as component A

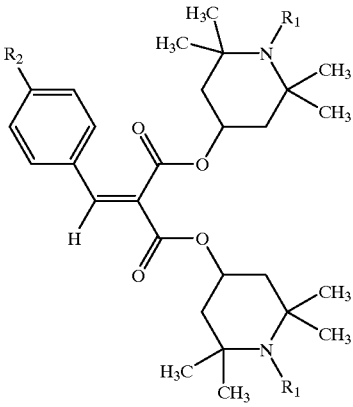 I wherein $R_1$ is hydrogen, hydroxyl, $C_{1-20}$alkyl, $C_{1-20}$alkoxy, or acyl, and $R_2$ is hydrogen, $C_{1-8}$alkyl, or $C_{1-2}$alkoxy, and a non-photoreactive, low molecular weight sterically hindered polyalkyl-piperidine as component B wherein component B is a compound of formula:

| | |
|---|---|
| $R_3$—OC(O)—$(CH_2)_n$—C(O)O—$R_3$ | B-1; |
| $R_3$—NH—$(CH_2)_n$—NH—$R_3$ | B-2; |
| $R_3$—OCH$_2$CH=CHCH$_2$—O—$R_3$ | B-3; |
| $R_3$—OC(O)—NR$_3$—$(CH_2)_6$—NR$_3$C(O)O—$R_3$ | B-4; |

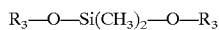 B-5;

wherein
R₃ is a group selected from the group consisting of:

(a)
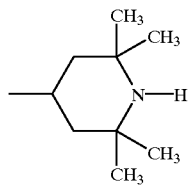

(b)
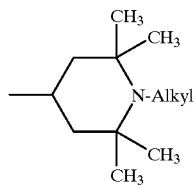

(c)
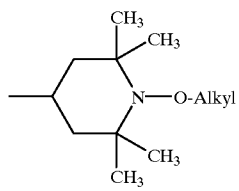

(d)
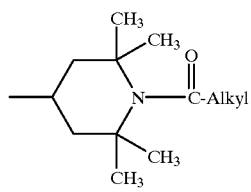

(e)
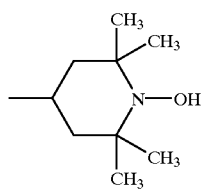

(f)
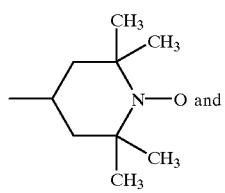

(g)
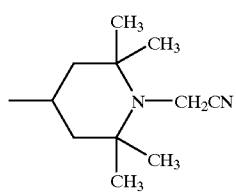

wherein
Alkyl is linear or branched or cyclic saturated $C_{1-18}$alkyl group or linear or branched or cyclic $C_{1-18}$ unsaturated group (alkenyl group), n is an integer from 0 to 20;

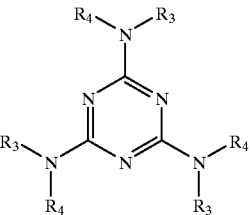 B-6 wherein
$R_4$ is hydrogen, $C_{1-20}$alkyl, or $R_3$;

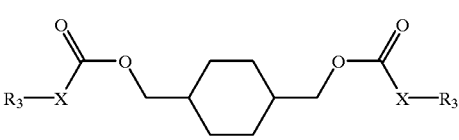 B-7 wherein
X is oxygen or N—$R_4$,

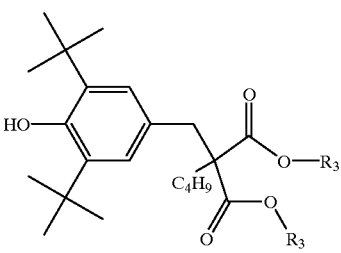 B-8

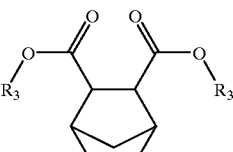 B-9

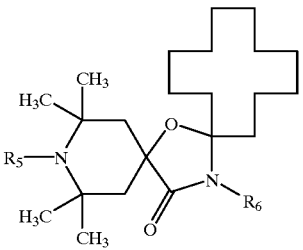 B-10 wherein
$R_5$ is hydrogen, $C_{1-20}$alkyl, hydroxyl, $C_{1-20}$alkoxy, or acyl,
$R_6$ is hydrogen, $C_{1-20}$alkyl,

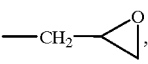, or $(CH_2)_mCOOR_7$, wherein m is an integer selected from 0 to 10, $R_7$ is $C_{1-20}$alkyl;

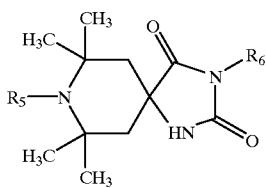 B-11

$R_3$—NH—C(O)—(CH$_2$)$_n$—C(O)—NH—$R_3$   B-12;

$R_3$—NR$_4$—(CH$_2$)$_m$COOR$_7$   B-13;

$R_3$—OC(O)CH$_2$CH[C(O)OR$_3$]CH[C(O)OR$_3$]CH$_2$C(O)O—$R_3$   B-14;

$R_3$—OC(O)(CH$_2$)$_n$—CH$_3$   B-15;

$R_3$OC(O)—Aryl   B-16;

$(R_3)_3$P   B-17;

$(R_3)_2$PR   B-18;

$R_3$PRR   B-19;

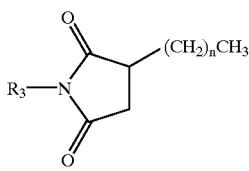 B-20

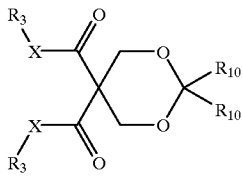 B-21

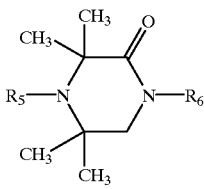 B-22 wherein
$R_{10}$ is hydrogen, $C_{1-10}$alkyl, or $C_{1-10}$alkenyl,
R is hydrogen, $C_{1-20}$alkyl, alkoxy, —C(O)alkyl, —OC(O)alkyl or

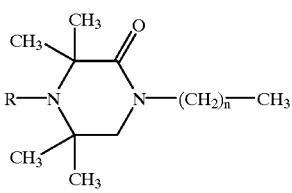

wherein n is an integer from 1 to 19;

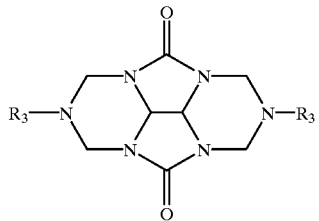 B-23 or $R_3$—O—CH=C(COOR$_3$)$_2$   B-24, and (b) a natural or synthetic polymeric or prepolymeric material which is identical to or compatible with a natural or synthetic polymeric substrate to be stabilized.

16. The process according to claim 14, wherein 0.01 to 7.5% by weight of the composition is added.

17. The process according to claim 15, wherein 0.01 to 7.5% by weight of the composition is added.

18. The process according to claim 16, wherein 0.03 to 5% by weight of the composition is added.

19. The process according to claim 18, wherein 0.2 to 3.5% by weight of the composition is added.

20. The process according to claim 17, wherein 0.03 to 5% by weight of the composition is added.

21. The process according to claim 20, wherein 0.2 to 3.5% by weight of the composition is added.

22. A stabilized organic material comprising:

(a) a composition consisting of a photoreactive, UV light absorbing, low molecular weight polyalkylpiperidine of formula I as component A

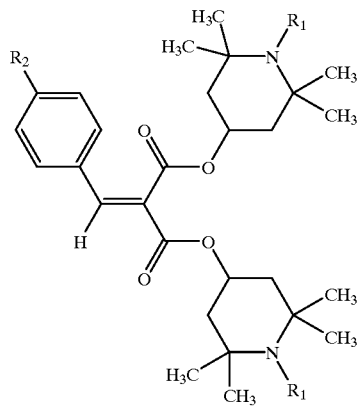 I wherein
$R_1$ is hydrogen, hydroxyl, $C_{1-20}$alkyl, $C_{1-20}$alkoxy, or acyl, and
$R_2$ is hydrogen, $C_{1-8}$alkyl, or $C_{1-2}$alkoxy,
and a non-photoreactive, low molecular weight sterically hindered polyalkyl-piperidine as component B wherein component B is a compound of formula:

$R_3$—OC(O)—(CH$_2$)$_n$—C(O)O—$R_3$   B-1;

$R_3$—NH—(CH$_2$)$_n$—NH—$R_3$   B-2;

$R_3$—OCR$_2$CH=CHCH$_2$—O—$R_3$   B-3;

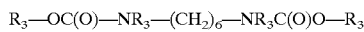  B-4;

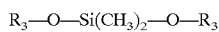  B-5;

wherein

R₃ is a group selected from the group consisting of:

(a)

(b)

(c)

(d)

(e)

(f)

(g)

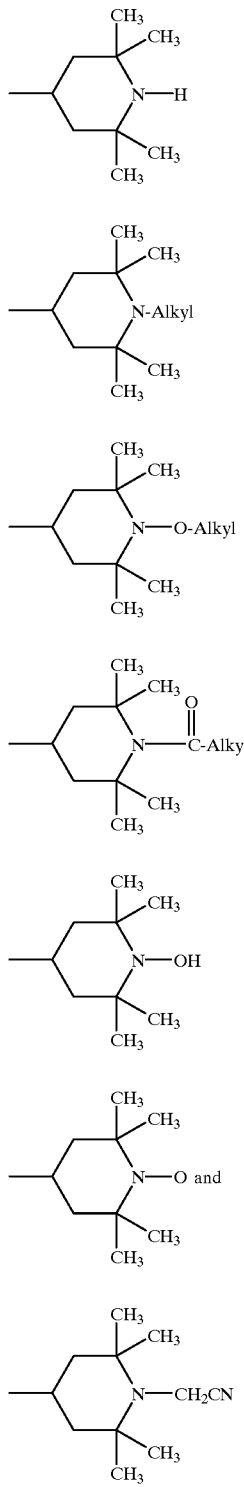

wherein

Alkyl is linear or branched or cyclic saturated $C_{1-8}$alkyl group or linear or branched or cyclic $C_{1-18}$ unsaturated group (alkenyl group), n is an integer from 0 to 20;

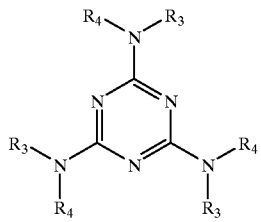  B-6 wherein $R_4$ is hydrogen, $C_{1-20}$alkyl, or $R_3$;

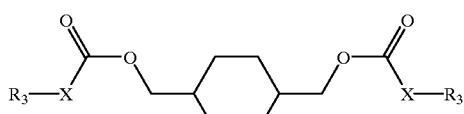  B-7 wherein

X is oxygen or N—$R_4$,

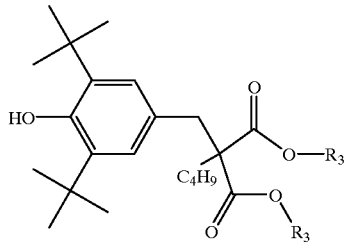  B-8

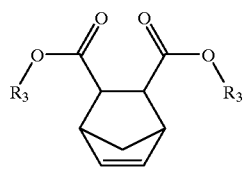  B-9

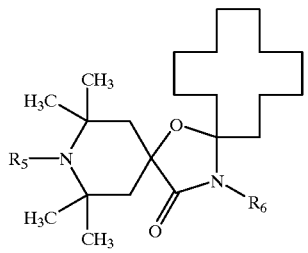  B-10 wherein $R_5$ is hydrogen, $C_{1-20}$alkyl, hydroxyl, $C_{1-20}$alkoxy, or acyl, $R_6$ is hydrogen, $C_{1-20}$alkyl,

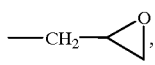

or $(CH_2)_mCOOR_7$, wherein m is an integer selected from 0 to 10, $R_7$ is $C_{1-20}$alkyl;

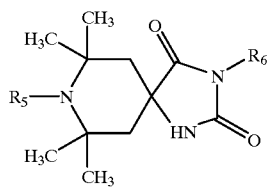
B-11

$R_3$—NH—C(O)—$(CH_2)_n$—C(O)—NH—$R_3$   B-12;

$R_3$—$NR_4$—$(CH_2)_m COOR_7$   B-13;

$R_3$—OC(O)$CH_2$CH[C(O)$OR_3$]CH[C(O)$OR_3$]$CH_2$C(O)O—$R_3$ B-14;

$R_3$—OC(O)$(CH_2)_n$—$CH_3$   B-15;

$R_3$OC(O)—Aryl   B-16;

$(R_3)_3$P   B-17;

$(R_3)_2$PR   B-18;

$R_3$PRR   B-19;

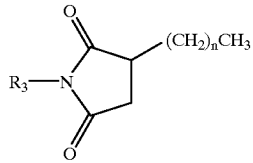
B-20

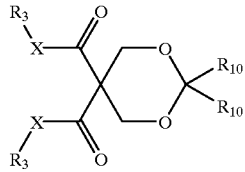
B-21

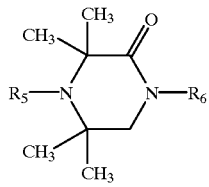
B-22 wherein
$R_{10}$ is hydrogen, $C_{1-10}$alkyl, or $C_{1-10}$alkenyl,
R is hydrogen, $C_{1-20}$alkyl, alkoxy, —C(O)alkyl, —OC(O)alkyl or

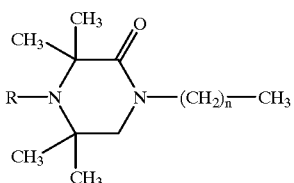

wherein n is an integer from 1 to 19;

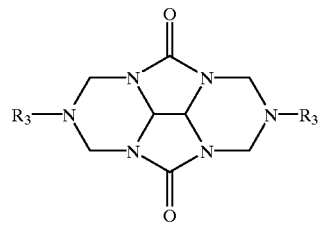
B-23 or $R_3$—O—CH=C(COO$R_3$)$_2$   B-24;

and (b) a natural or prepolymeric substrate.

23. A method of using a stabilized organic material in the production of fibers, yarn, moldings, foamed plastic, coatings, lacquers, varnishes, adhesives, and fabric comprising shaping the stabilized organic material wherein the stabilized organic material comprises:

(a) a composition consisting of a photoreactive, UV light absorbing, low molecular weight polyalkylpiperidine of formula I as component A

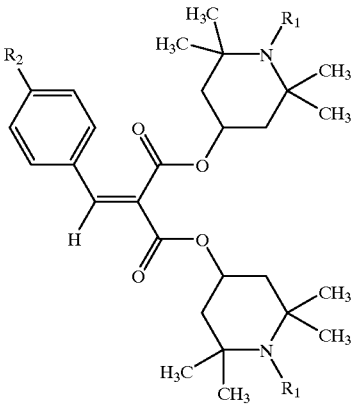
I wherein
$R_1$ is hydrogen, hydroxyl, $C_{1-20}$alkyl, $C_{1-20}$alkoxy, or acyl, and
$R_2$ is hydrogen, $C_{1-8}$alkyl, or $C_{1-2}$alkoxy,
and a non-photoreactive, low molecular weight sterically hindered polyalkyl-piperidine as component B wherein component B is a compound of formula:

$R_3$—OC(O)—$(CH_2)_n$—C(O)O—$R_3$   B-1;

$R_3$—NH—$(CH_2)_n$—NH—$R_3$   B-2;

$R_3$—OCH$_2$CH=CHCH$_2$—O$R_3$   B-3;

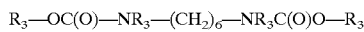   B-4;

   B-5;

wherein

R₃ is a group selected from the group consisting of:

(a)
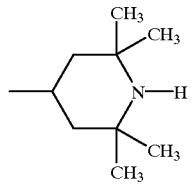

(b)
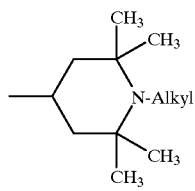

(c)
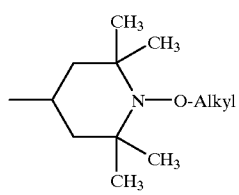

(d)
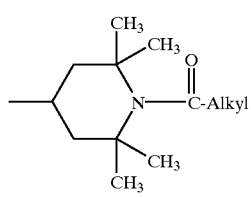

(e)
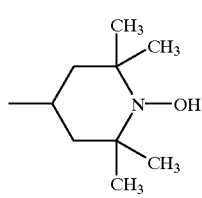

(f)
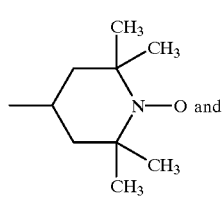

(g)
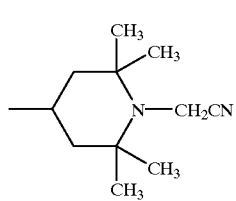

wherein

Alkyl is linear or branched or cyclic saturated $C_{1-8}$alkyl group or linear or branched or cyclic $C_{1-18}$ unsaturated group (alkenyl group), n is an integer from 0 to 20;

B-6
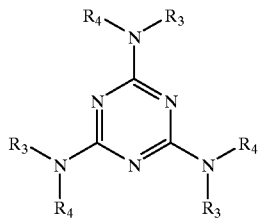

wherein $R_4$ is hydrogen, $C_{1-20}$alkyl, or $R_3$;

B-7
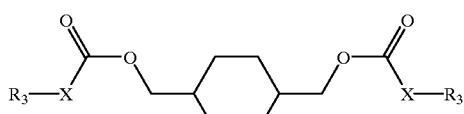

wherein

X is oxygen or N—$R_4$,

B-8
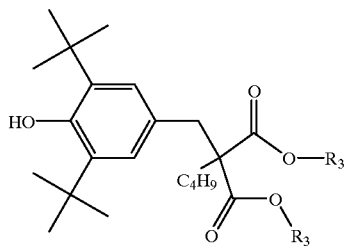

B-9
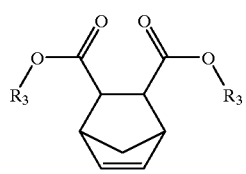

B-10
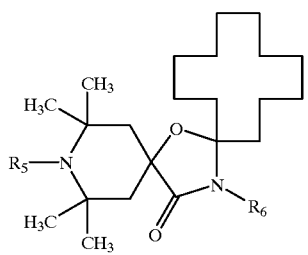

wherein $R_5$ is hydrogen, $C_{1-20}$alkyl, hydroxyl, $C_{1-20}$alkoxy, or acyl, $R_6$ is hydrogen, $C_{1-20}$alkyl,

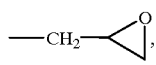

or $(CH_2)_mCOOR_7$, wherein m is an integer selected from 0 to 10, $R_7$ is $C_{1-20}$alkyl;

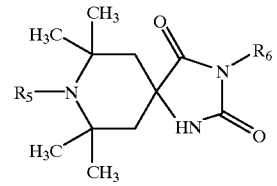
B-11

$R_3$—NH—C(O)—$(CH_2)_n$—C(O)—NH—$R_3$    B-12;

$R_3$—$NR_4$—$(CH_2)_m$COOR$_7$    B-13;

$R_3$—OC(O)CH$_2$CH[C(O)OR$_3$]CH[C(O)OR$_3$]CH$_2$C(O)O—$R_3$    B-14;

$R_3$—OC(O)$(CH_2)_n$—CH$_3$    B-15;

$R_3$OC(O)—Aryl    B-16;

$(R_3)_3P$    B-17;

$(R_3)_2PR$    B-18;

$R_3PRR$    B-19;

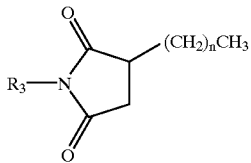
B-20

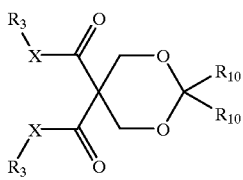
B-21

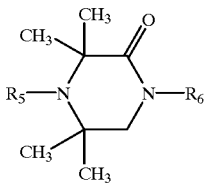
B-22 wherein $R_{10}$ is hydrogen, $C_{1-10}$alkyl, or $C_{1-10}$alkenyl,

R is hydrogen, $C_{1-20}$alkyl, alkoxy, —C(O)alkyl, —OC(O)alkyl or

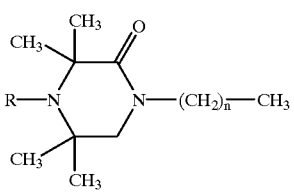

wherein n is an integer from 1 to 19;

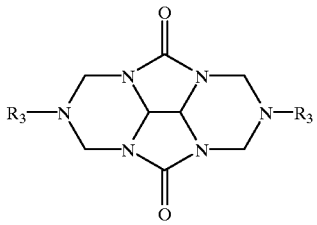
B-23 or $R_3$—O—CH=C(COOR$_3$)$_2$    B-24;

and (b) a natural or prepolymeric substrate.

* * * * *